(12) United States Patent
Li et al.

(10) Patent No.: US 8,884,007 B2
(45) Date of Patent: Nov. 11, 2014

(54) HEXENONE COMPOUNDS AND MEDICAL USE THEREOF

(75) Inventors: Song Li, Beijing (CN); Wu Zhong, Beijing (CN); Juan Liu, Beijing (CN); Lili Wang, Beijing (CN); Kunlun He, Beijing (CN); Long Long, Beijing (CN); Junhai Xiao, Beijing (CN); Zhibing Zheng, Beijing (CN); Wei Li, Beijing (CN); Xin Li, Beijing (CN); Guoliang Hu, Beijing (CN)

(73) Assignee: Institute of Pharmacology and Toxicology Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 13/696,697

(22) PCT Filed: May 16, 2011

(86) PCT No.: PCT/CN2011/000848
§ 371 (c)(1),
(2), (4) Date: Jan. 18, 2013

(87) PCT Pub. No.: WO2011/140832
PCT Pub. Date: Nov. 17, 2011

(65) Prior Publication Data
US 2013/0116256 A1 May 9, 2013

(30) Foreign Application Priority Data
May 14, 2010 (CN) .......................... 2010 1 0172482

(51) Int. Cl.
*C07D 295/215* (2006.01)
*C07D 295/194* (2006.01)
(52) U.S. Cl.
CPC ........ *C07D 295/215* (2013.01); *C07D 295/194* (2013.01)
USPC ...................................... 544/160; 514/237.8
(58) Field of Classification Search
CPC .................................................. C07D 295/215
USPC ........................................ 544/160; 514/237.8
See application file for complete search history.

(56) References Cited

U.S. PATENT DOCUMENTS

| 5,041,679 A | 8/1991 | Hiratsuka et al. |
| 2007/0142465 A1 | 6/2007 | Umezawa et al. |

FOREIGN PATENT DOCUMENTS

CN 1852709 A 10/2006

OTHER PUBLICATIONS

Ziedan et al. (European Journal of Medicinal Chemistry, 45 (2010), p. 4523-4530).*
Kubinyi (3D QSAR in Drug Design: Ligand-Protein Interactions and Molecular Similarity, vol. 2-3, Springer, 1998, 800 pages). pp. 243-244 provided.*
Wermuth, The Practice of Medicinal Chemsitry, 2d ed. (2003), 768 pages. Chs. 9-10 provided.*
International Search Report for PCT/CN2011/000848 mailed Aug. 25, 2011.
Supplemental Search Report for EP 11780054 mailed Oct. 29, 2013, 5 pages.
Goerdeler, et al., "Umsetzung von Kohlensaureester-isothiocyanaten mit Iminen verschiedenen Typs zu cyclischen and linearen Addukten", Chem. Ber., vol. 116, 1983, pp. 1297-1308, XP002713122.
Beilstein Institute for Organic Chemistry, Frankfurt-Main, DE; 2002, XP002713123, vol. 177, No. 12, 1 page.

\* cited by examiner

*Primary Examiner* — Robert Havlin
(74) *Attorney, Agent, or Firm* — Roberts Mlotkowski Safran & Cole, P.C.

(57) ABSTRACT

The present invention relates to a compound of Formula I, or an isomer, pharmaceutically acceptable salt and solvate thereof; to a composition comprising a compound of Formula I, or an isomer, pharmaceutically acceptable salt and solvate thereof, and a pharmaceutically acceptable carrier, excipient or diluent; and also to use of a compound of Formula I, or an isomer, pharmaceutically acceptable salt and solvate thereof for combating apoptosis, or preventing or treating a disease or disorder associated with apoptosis; and especially use for protecting cardiomyocyte, or preventing or treating a disease or disorder associated with cardiomyocyte apoptosis.

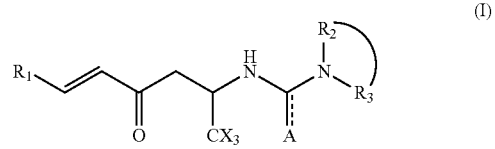

5 Claims, No Drawings

US 8,884,007 B2

HEXENONE COMPOUNDS AND MEDICAL USE THEREOF

RELATED APPLICATIONS

This application is a national stage application of PCT/CN2011/000848 filed May 16, 2011, which claims priority to CN Application No. 201010172482.0, filed May 14, 2010, the entire contents and disclosures of which are hereby incorporated by reference.

TECHNICAL FIELD

The present invention relates to the field of medicinal chemistry, and specifically to a hexenone compound and a pharmaceutical composition thereof. The present invention also relates to use of the compounds and pharmaceutical compositions thereof for combating apoptosis, prophylaxis or treatment of a disease or disorder associated with apoptosis, and especially for protecting myocardial cells and for prophylaxis or treatment of a disease or disorder associated with apoptosis of myocardial cells.

BACKGROUND ART

Apoptosis usually refers to programmed cell death of body cells occurred via the regulation of intracellular genes and products thereof during development process or under the action of some factors. Apoptosis commonly exists in biosphere under both physiological state and pathological state. It plays important roles in embryo development and morphogenesis, stability of normal cells in tissues, defense and immune reaction of body, cell damage caused by diseases or poisoning, ageing, generation and development of tumors, and is one of the hottest spots in biomedical research.

Some researches show that the occurrence of many serious diseases relates to the over apoptosis of cells, for example, the reduction of $CD4^+$ T cells during the development of ADIS; the cell death mediated by cytotoxic T cell during transplant rejection reaction; the apoptosis of myocardial cells and nerve cells of ischemia and reperfusion injury; nervous system degradation diseases (such as Alzheimer disease, Parkinson's disease, etc.); apoptosis caused by exposure to ionizing radiation in many tissues.

Some evidences have indicated that cardiomyocytes apoptosis closely associates with the occurrence, development and prognosis of many heart diseases. It is found in the research about cardiomyocytes apoptosis that the infarct of cardiac muscle is not equivalent to myocardial necrosis, and apoptosis is one of mechanisms of myocardial infarction, and is the main manner of myocardial death of early infarction and myocardial death caused by ischemia/reperfusion, and the apoptosis of cardiomyocytes in large amount at this time aggravates myocardial damage. In 1989, Nepomniashchikh et al found in the observation of ultrastructure of hunger myocardial atrophy that the synthesis of cardiomyocytes structural protein decreased, and the cell number decreased but was not accompanied with a proportional decrease of cell nucleus, an thus preliminarily proposed that hunger myocardial atrophy was caused by apoptosis. In 1994, Gottlieb and Kawano et al obtained direct evidences of cardiomyocytes apoptosis by using electron microscope in combination with DNA gel electrophoresis, in which the former disclosed reperfusion injury induced rabbit cardiomyocytes apoptosis, and the latter confirmed that myocarditis patients had concomitant cardiomyocytes apoptosis. Tanaka et al also confirmed the existence of apoptosis of cardiomyocytes in suckling mice. With the progress of methodology and research of apoptosis, pathological functions of cardiomyocytes apoptosis have been found in many heart diseases. Some researches indicate the heart injury in spontaneously hypertensive rat (SHR) is relevant to apoptosis; the conversion from cardiac pachynsis to heart failure in advanced stage is caused by cardiomyocytes apoptosis; acute myocardial infarction also induces apoptosis in early stage of infarction and reperfusion injury, except necrosis; cardiomyocytes apoptosis is also found in transplanted heart and right ventricular maldevelopment myocardial diseases, and anoxia also induces cardiomyocytes apoptosis.

Apoptosis has recoverability in some extents, and the apoptosis in myocardial infarction and ischemia/reperfusion has its own features and regular patterns, so that the features may be used for prevention and reduction of apoptosis and may provide enlightenments for clinical prophylaxis of ischemia/reperfusion injury; during the process of reperfusion, the apoptosis occurred in contraction band region (around infarction site) is induced by some precipitating factors, so that the inhibition factors of apoptosis such as drugs may be used for preventing apoptosis and treating corresponding diseases caused by apoptosis.

However, there are few kinds and numbers of drugs so far that can be clinically used for combating apoptosis and protecting cells, and their selectivity and targeting property are not satisfied, and therefore it is of great significance to continuously develop new, safe and effective drugs for combating apoptosis and protecting cells, and especially drugs with a novel mechanism of action.

CONTENTS OF THE INVENTION

In order to develop new, safe and effective drugs for combating apoptosis and protecting cells, after conducting extensive experimental researches for a long term the inventors have found a group of hexenone compounds that have effects of combating apoptosis and protecting myocardial cells, and can be used for prophylaxis or treatment of diseases or disorders associated with cardiomyocyte apoptosis. Specifically, the first aspect of the present invention relates to a compound of Formula I, or an isomer, pharmaceutically acceptable salt or solvate thereof.

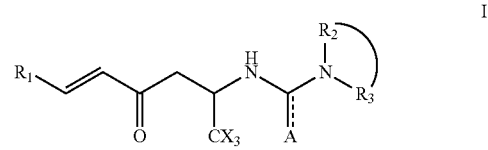

I wherein
A represents =S, —$SR_4$ or =O;
X represents F, Cl, Br or I;
$R_1$ represents phenyl; a phenyl-$C_1$-$C_6$ alkyl-, wherein the phenyl is unsubstituted or substituted with 1-4 (e.g., 1-2, 1, 2, 3 or 4) substituents independently selected from the group consisting of: halogen, nitro, hydroxyl, amino, cyano, $C_1$-$C_6$ alkyl, $C_1$-$C_6$ alkoxy, and $C_1$-$C_6$ haloalkyl, wherein the alkyl, alkoxy and haloalkyl may be optionally substituted with hydroxyl, —O—($C_1$-$C_4$)-alkyl, oxo, amino, —NH—($C_1$-$C_4$)-alkyl, or —N—[($C_1$-$C_6$)-alkyl]$_2$, or the alkyl, alkoxy and haloalkyl are optionally intervened by —O—, —S—, —NH—, —COO—, or —CONH—; a 5- or 6-membered heterocyclic ring; or a substituted heterocyclic ring, wherein the heterocyclic ring is unsubstituted or substituted with 1-3 (e.g., 1-2, 1, 2, or 3) substituents independently selected from the group consisting of: halogen, nitro, hydroxyl, amino, cyano, $C_1$-$C_6$ alkyl, $C_1$-$C_6$ alkoxy, and $C_1$-$C_6$ haloalkyl, wherein the alkyl, alkoxy and haloalkyl may be optionally substituted with hydroxyl, —O—($C_1$-$C_4$)-alkyl, oxo, amino, —NH—($C_1$-$C_4$)-alkyl, or —N—[($C_1$-$C_6$)-alkyl]$_2$, or the alkyl, alkoxy and haloalkyl are optionally intervened by —O—, —S—, —NH—, or —COO— and the heterocyclic ring may be a nitrogen nitrogen heterocyclic ring, nitrogen oxygen heterocyclic ring, or nitrogen sulfur heterocyclic ring;

$R_2$, and $R_3$ represent hydrogen, $C_1$-$C_6$ alkyl, $C_3$-$C_6$ cycloalkyl, substituted $C_3$-$C_6$ cycloalkyl, $C_1$-$C_6$ alkoxy$C_1$-$C_6$ alkyl, amino $C_1$-$C_6$ alkyl, mono-substituted or di-substituted amino $C_1$-$C_6$ alkyl, phenyl $C_1$-$C_6$ alkyl, substituted phenyl $C_1$-$C_6$ alkyl, heterocyclic $C_1$-$C_6$ alkyl, substituted heterocyclic $C_1$-$C_6$ alkyl, phenyl, substituted phenyl, or a $C_1$-$C_6$ heterocyclic or substituted $C_1$-$C_6$ heterocyclic group, wherein $R_2$ and $R_3$ may be attached together to form a ring; and $R_4$ represents a $C_1$-$C_6$ alkyl.

Preferably, the compound of the present inventions is a compound of Formula (I), or an isomer, pharmaceutically acceptable salt and solvate thereof, wherein:

A represents =S, —$SR_4$ or =O;

X represents F, Cl, Br or I;

$R_1$ represents phenyl; phenyl-$C_1$-$C_6$ alkyl-, wherein the phenyl is unsubstituted or substituted with 1-4 (e.g., 1-2, 1, 2, 3 or 4) substituents independently selected from the group consisting of: halogen, nitro, hydroxyl, amino, cyano, $C_1$-$C_6$ alkyl, $C_1$-$C_6$ alkoxy, and $C_1$-$C_6$ haloalkyl, wherein the alkyl, alkoxy and haloalkyl may be optionally substituted with hydroxyl, —O—($C_1$-$C_4$)-alkyl, oxo, amino, —NH—($C_1$-$C_4$)-alkyl, or —N—[($C_1$-$C_6$)-alkyl]$_2$, or the alkyl, alkoxy and haloalkyl are optionally substituted with —O—, —S—, —NH—, —COO—, or —CONH—; thienyl; thiazolyl, wherein the thienyl, and thiazolyl is unsubstituted or substituted with 1-3 (e.g., 1-2, 1, 2, or 3) substituents independently selected from the group consisting of: halogen, nitro, hydroxyl, amino, cyano, $C_1$-$C_6$ alkyl, $C_1$-$C_6$ alkoxy, and $C_1$-$C_6$ haloalkyl, wherein the alkyl, alkoxy and haloalkyl may be optionally substituted with hydroxyl, —O—($C_1$-$C_4$)-alkyl, oxo, amino, —NH—($C_1$-$C_4$)-alkyl, or —N—[($C_1$-$C_6$)-alkyl]$_2$, or the alkyl, alkoxy and haloalkyl are optionally intervened by —O—, —S—, —NH—, or —COO—;

$R_2$, and $R_3$ represent hydrogen, $C_1$-$C_6$ alkyl, $C_3$-$C_6$ cycloalkyl, substituted $C_3$-$C_6$ cycloalkyl, $C_1$-$C_6$ alkoxy$C_1$-$C_6$ alkyl, amino $C_1$-$C_6$ alkyl, mono-substituted or di-substituted amino $C_1$-$C_6$ alkyl, phenyl $C_1$-$C_6$ alkyl, substituted phenyl $C_1$-$C_6$ alkyl, heterocyclic $C_1$-$C_6$ alkyl, phenyl, substituted phenyl, or a heterocyclic or substituted heterocyclic group, wherein $R_2$ and $R_3$ may be attached together to form a saturated cycloalkyl, nitrogen- or oxygen-containing heterocyclic ring; and $R_4$ represents methyl, ethyl, propyl, isopropyl, butyl or pentyl.

In particular, the compound of the present invention is preferably a compound of Formula (I), or an isomer, pharmaceutically acceptable salt and solvate, wherein:

A represents =S, —$SR_4$ or =O;

X represents Cl;

$R_1$ represents phenyl or 2-thienyl;

$R_2$, and $R_3$ represent hydrogen, methyl, isopropyl, 2-methoxyethyl, 3-isopropoxypropyl, 2-N,N-dimethylethyl, cyclohexyl, cycloheptyl, orth-methoxyphenyl, orth-fluorophenyl, orth-chlorophenyl, para-chlorophenyl, benzyl or 8-quinolyl, wherein $R_2$ and $R_3$ may be attached together to form piperidine, morpholine or N-methylpiperazine ring; and $R_4$ represents methyl or ethyl.

Particularly, the compound of Formula (I) is preferably the following compound:

(1E)-1-phenyl-5-(1-morpholinylthiocarboxamido)-6,6,6-trichloro-1-ene-3-hexanone, or an isomer, pharmaceutically acceptable salt and solvate thereof.

The compound of Formula (I) of the present invention can be prepared by the following method:

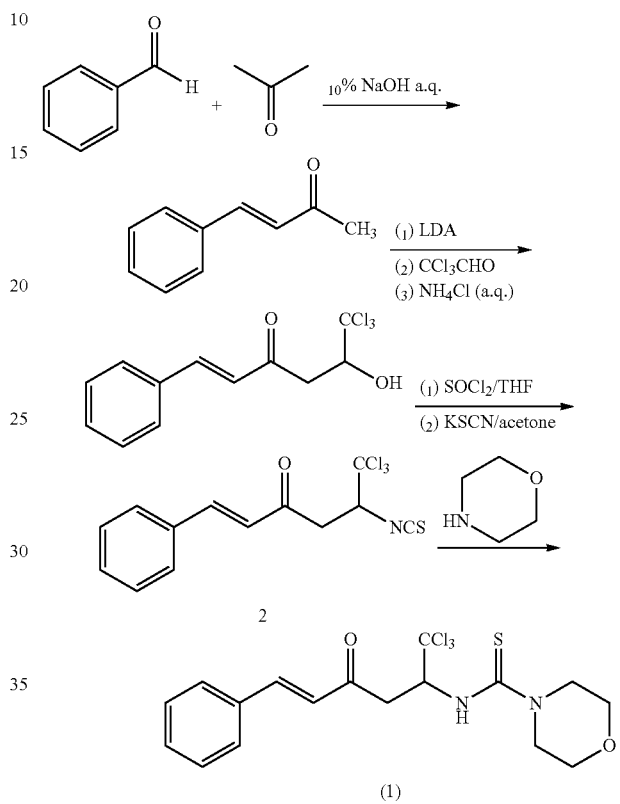

By taking Compound (1) as example, the compound of the present invention is synthesized using benzaldehyde as a starting material, by reacting benzaldehyde with acetone in a solution of sodium hydroxide in methanol to generate (1E)-1-phenyl 1-ene-3-acetone, which is then reacted with trichloroacetaldehyde under the catalysis of LDA to obtain intermediate 1, chloridizing intermediate 1 with thionyl chloride and then reacting it with potassium thiocyanate to obtain intermediate 2, and finally refluxing intermediate 2 with morpholine in tetrahydrofuran to obtain the Compound (1).

Another aspect of the present invention relates to a pharmaceutical composition comprising a compound of Formula (I), or an isomer, pharmaceutically acceptable salt and solvate thereof, and an excipient or a diluent.

The present invention further relates to use of the compound of Formula (I) or an isomer, pharmaceutically acceptable salt and solvate thereof according to the first aspect of the present invention for the manufacture of a medicament for combating apoptosis, or preventing or treating a disease or disorder associated with apoptosis.

The present invention further relates to a use of the compound of Formula (I) or an isomer, pharmaceutically acceptable salt and solvate thereof according to the first aspect of the present invention for the manufacture of a medicament for protecting cardiomyocytes and preventing or treating a disease or disorder associated with cardiomyocyte apoptosis.

The present invention further relates to a method for combating apoptosis, or preventing or treating a disease or disorder associated with apoptosis, the method comprising administering a subject in need thereof a therapeutically effective amount of a compound of Formula (I) or an isomer, pharmaceutically acceptable salt and solvate thereof according to the first aspect of the present invention.

The present invention further relates to a method for protecting cardiomyocyte, or preventing or treating a disease or disorder associated with cardiomyocyte apoptosis, the method comprising administering a subject in need thereof a therapeutically effective amount of a compound of Formula (I) or an isomer, pharmaceutically acceptable salt and solvate thereof.

The disease or disorder associated with apoptosis according to the present invention comprises: cardiovascular diseases, nerve degenerative diseases, multiple sclerosis, viral infections, etc.

The disease or disorder associated with cardiomyocyte apoptosis according to the present invention includes but is not limited to: (i) hunger myocardial atrophy, (ii) myocarditis, (iii) heart failure, (iv) myocardial damage caused by primary hypertension, (v) myocardial damage caused by early stage of acute myocardial infarction, (vi) myocardial damage caused by acute myocardial infarction reperfusion, (vii) pathological changes of cardiomyocytes caused by heart transplantation, or (viii) displastic mycocardiosis; or cardiomyocytes apoptosis caused by anoxia, or sclerosis in cardiovascular system.

According to the present invention, the term "heterocyclic ring" includes but is not limited to: pyridine, pyrrole, furan, thiophene, pyrazole, imidazole, thiazole, oxazole, isoxazole, indole, benzofuran, benzimidazole, carbazole, pyridazine, pyrimidine, pyrazine, quinoline, isoquinoline, purine, phenothiazine, and phenazine.

Those skilled in the art would appreciate that the compound of Formula I has a chiral center. When a single enantiomer of the compound of Formula I is required, it can be prepared by using reactants present in single enantiomer form in all possible steps, or prepared by performing reaction in the presence of an reagent or catalyst in single enantiomer form, or prepared by resolution of a mixture of stereoisomers via conventional methods. Some preferable methods comprises resolution using microorganisms, resolution and chiral acid such as any usable acid for example mandelic acid, camphor sulfonic acid, tartaric acid, lactic acid, etc. form diastereomer salt, or resolution and chiral base such as bracine, cinchona alkaloid or derivatives thereof form diastereomer salt. The commonly used methods can be seen in "Enantiomers, Racemates and Resolution" as edited by Jaques et al (Wiley Interscience, 1981).

Those skilled in the art should appreciate that the compound of the present invention can also be used in form of its pharmaceutically acceptable salt or solvate. The physiologically acceptable salts of the compound of Formula I include conventional salts formed with pharmaceutically acceptable inorganic acid or organic acid or inorganic base or organic base and acid addition salt of quaternary ammonium. More specific examples of suitable acid salts include salts of hydrochloric acid, hydrobromic acid, sulfuric acid, phosphoric acid, nitric acid, perchloric acid, fumaric acid, acetic acid, propionic acid, succinic acid, hydroxyacetic acid, formic acid, lactic acid, maleic acid, tartaric acid, citric acid, pamoic acid, malonic acid, hydroxymaleic acid, phenylacetic acid, glutamic acid, benzoic acid, salicylic acid, fumaric acid, toluene sulfonic acid, methylsulfonic acid, naphthalene-2-sulfonic acid, benzene sulfonic acid, hydroxynaphthoic acid, hydroiodic acid, malic acid, steroic, tannic acid, etc. As for other acids, such as oxalic acid, although they per se are not pharmaceutically acceptable, they can be used for prepare salts as intermediates to obtain the compound of the present invention and pharmaceutically acceptable salts thereof. More specific suitable alkali salts include salts of sodium, lithium, potassium, magnesium, aluminum, calcium, zinc, N,N'-dibenzylethylenediamine, chloroprocaine, choline, diethanolamine, ethylenediamine, N-methylglucosamine, and procaine. The compounds of the present invention as mentioned thereafter include the compound of Formula I and a pharmaceutically acceptable salt and solvate thereof.

The present invention further comprises a prodrug of the compound of the present invention, and once the prodrug is administered, it is chemically converted via metabolic procedure into an active drug. In general, this kind of prodrug is a functional derivative of the compound of the present invention, which can be readily converted into the needed compound of Formula (I). For example, "Design Of Prodrugs", edited by H Bund Saard, Elsevier, 1985, describes conventional methods of selecting and preparing suitable prodrug derivatives.

The present invention also includes any active metabolites of the compound of the present invention.

Another aspect of the present invention relates to a pharmaceutical composition comprising a racemic or optical isomer of the compound of the present invention, and at least one pharmaceutically acceptable carrier, and being useful in in vivo treatment and having biocompatibility. The pharmaceutical composition can be processed into various forms for different administration routes. The compound of the present invention can also be processed into various pharmaceutically acceptable salts.

The pharmaceutical composition of the present invention comprises an effective amount of the compound of Formula I of the present invention or a pharmaceutically acceptable salt or hydrate thereof and one or more suitable pharmaceutically acceptable carriers. The pharmaceutically acceptable carriers comprise but are not limited to: ion exchangers, alumina, aluminum stearate, lecithin, serum protein such as human albumin, buffering substance such as phosphate, glycerol, sorbic acid, potassium sorbate, mixture of partial glycerides of saturated plant fatty acids, water, salts or electrolytes, such as protamine sulfate, disodium hydrogen phosphate, potassium hydrogen phosphate, sodium chloride, zinc salt, colloid silica, magnesium trisilicate, polyvinylpyrrolidone, cellulose substances, polyethylene glycol, sodium carboxymethylcellulose, polyacrylates, beeswax, and lanolin.

The pharmaceutical composition of the compound of the present invention can be administered by any of the following manners: oral administration, spray inhalation, rectal administration, nasal administration, bucca administration, local administration, parenteral administration, such as subcutaneous, intravenous, intramuscular, intraperitoneal, intrathecal, intraventricular, intrasternal, intracranial injection or perfusion, or administration with aid of an explanted reservoir, preferably oral administration, intraperitoneal or intravenous administration.

For oral administration, the compound of the present invention can be processed in any acceptable forms for oral administration, including but not being limited to tablets, capsules, water solutions or water suspensions. The tablets use a carrier generally comprising lactose and maize starch, additionally comprising a lubricant such as magnesium stearate. The capsules use a diluent generally comprising lactose and dry maize starch. The water suspensions usually use a mixture of an active component and suitable emulsifying agent and suspending agent. If necessary, the above oral dosage forms can further comprise some sweetening agents, flavoring agents or coloring agents.

For local administration, especially in treatment of neurogenic disease of a readily accessible affected surface or organ such as eye, skin or inferior part of intestinal tract by local external application, the compound of the present invention can be processed into different dosage forms for local administration according to different affected surfaces or organs, which are illustrated as follows:

For local administration to eyes, the compound of the present invention can be processed in a dosage form of micronized suspension or solution, in which the used carrier is isotonic sterile saline with a certain pH, wherein a preservative such as chlorobenzylalkanol salt can be added or not be added. For the eye use, the compound can be processed into ointment form, such as Vaseline ointment.

For local administration to skin, the compound of the present invention can be processed in suitable dosage forms such as ointments, lotions or creams, wherein the active component is suspended or dissolved in one or more carriers. The carriers usable in ointments include but are not limited to: mineral oil, liquid paraffin, white Vaseline, propylene glycol, polyethylene oxide, polypropylene oxide, emulsified wax and water; the carriers usable in lotions or creams comprise but are not limited to: mineral oil, sorbitan monostearate, Tween 60, hexadecane ester wax, hexadecylene aromatic alcohol, 2-octyldodecanol, benzyl alcohol and water.

The compound of the present invention can further be administered in dosage form of sterile injections, including water or oil suspensions for sterile injection, or sterile injection solutions. The usable carriers and solvents include water, Ringer's solution and isotonic sodium chloride solution. In addition, sterile nonvolatile oil can also be used as solvent or suspending medium, such as monoglyceride or diglyceride.

It should be further pointed out that the dose and usage method of the compound of the present invention depend on many factors, including age, body weight, gender, natural health status, nutritional status, activity of compound, administration time, metabolic rate, severity of disease and subjective judgment of diagnostic doctor.

BENEFICIAL EFFECTS OF THE INVENTION

The present invention provides a group of hexenone compounds, and has demonstrated such compounds have effects of combating apoptosis and protecting cells, and thus provides a new method and approach for the treatment of diseases or disorders caused by apoptosis, and especially for the treatment of diseases or disorders caused by cardiomyocytes apoptosis.

SPECIFIC MODES FOR CARRYING OUT THE INVENTION

The embodiments of the present invention are illustrated as follows in combination with the following examples, but those skilled in the art would understand that the following examples are merely to illustrate the present invention and should not be construed as a restriction of the present invention. The procedures in the examples which are not given in detail are performed according to the conventional conditions, or the conditions suggested by manufacturers. The reagents or instruments which manufacturers are not given are all conventional products commercially available.

The melting points of compounds were measured by RY-1 melting point instrument, and thermometers were not calibrated. Mass spectrums were measured by Micromass Zab-Spec high resolution mass spectrometer (resolution: 1000). $^1$H NMR was measured by JNM-ECA-400 superconducting NMR meter, working frequency: $^1$H NMR 400 MHz, $^{13}$C NMR 100 MHz.

EXAMPLE 1

(1E)-1-phenyl-5-(1-morpholinylthiocarboxamido)-6,6,6-trichloro-1-ene-3-hexanone

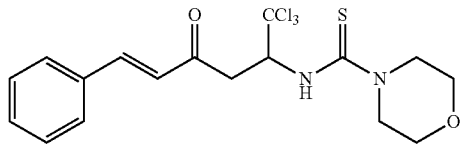

3 ml of acetone was added to 4.80 g of 10% NaOH aqueous solution, and the mixture was stirred at 30° C. for 5 minutes, added dropwise with 1 ml of benzaldehyde, and stirred at room temperature for 3 h. After reaction solution was layered, and the organic layer was eluted with petroleum ether:ethyl actate=20:1 as the developing agent to obtain 1.00 g of (1E)-1-phenyl-1-ene-3-butanone as a yellow crystal. 0.64 g of diisopropylamine was dissolved in 10 ml THF under protection of nitrogen gas, and the solution was cooled to −40° C., added dropwise with 0.40 g of n-butyl lithium, stirred for 30 minutes and then cooled to −78° C. 0.84 g of (1E)-1-phenyl-1-ene-3-butanone was dissolved in 15 ml THF, and the solution was added dropwise to a LDA solution, and then reacted at −78° C. for 40 min. 1.19 g of trichloroacetaldehyde was dissolved in 15 ml THF, and the solution was added dropwise with the above reaction solution, and then reacted at −78° C. for 12 h. After the temperature was elevated to −40° C., the reaction was added with 20 ml of saturated NH$_4$Cl aqueous solution, stirred for 30 min, heated to room temperature and then added with 20 ml of ethyl acetate for extraction. The organic layer was eluted with petroleum ether:ethyl acetate=6:1 as the developing agent to obtain 1.49 g of (1E)-1-phenyl-5-hydroxyl-6,6,6-trichloro-1-ene-3-hexanone as a light yellow crystal. It was dissolved in 20 ml THF, and the solution was added with 1.1 ml of thionyl chloride, and refluxed for 6 h. The reaction solvent was evaporated, and the residue was dissolved in 20 ml of acetone, then added with 0.74 g of KSCN, and stirred at 40° C. for 1.5 h. Petroleum ether:ethyl acetate=30:1 was used as the developing agent for elution after the end of reaction to obtain 1.2 g of (1E)-1-phenyl-5-isothiocyanate-6,6,6-trichloro-1-ene-3-hexanone as a light yellow solid. 0.33 g of the solid and 0.06 ml of morpholine were refluxed in THF for 1 h to precipitate a white solid, which was recrystallized from THF to obtain 0.10 g of the pure product. $^1$H-NMR (400 MHz, DMSO-d$_6$) δ 3.28-3.43 (m, 4H); δ 3.46-3.58 (m, 4H); δ 3.68-3.74 (m, 2H); δ 3.81-3.87(m, 2H); δ 6.27-6.29(m, 1H); δ 7.02-7.06(d, 1H); δ 7.43-7.46(t, 3H); δ 7.60-7.64(d, 1H); δ 7.21-7.74(m, 2H); δ 8.03-8.05(d, 1H). MS (TOF) 421.7 (M+).

EXAMPLE 2

Experiment on the Activity of the Compound for Protection of Cardiomyocyte

Primary Culture of Cardiomyocyte

The isolation and culture of cardiomyocytes were performed by referring to the differential adhesion method (Kreider, A. Messing, H. Doan, S. U. Kim, R. P. Lisak and D. E. Pleasure, Enrichment of Schwann cell cultures from neonatal rat sciatic nerve by differential adhesion, *Brain Res* 2 (1981), pp. 433-444). Wistar sucking mice newborn within 24 h were used, sterilized at skin of ventrum with iodine tincture and ethanol, subjected to thoracotomy using scissors at subxiphoid median line with a deviation to left, heart was taken out after slant thoracotomy and placed in PBS precooled with ice; the heart was softly blown and beaten with 0.01M PBS to remove blood cells and other tissues, then cut into pieces with 0.5 $mm^3$ size, washed with 0.01M PBS repeatedly for 2-3 times; the pieces were placed in conical flask, added with 4 ml of 0.125% pancretin, 1 ml of 0.1% collagenase II (final concentrations separately being 0.1% and 0.02%), shaken in 37° C. water bath for 10 min, the supernatant was discarded; then 4 ml of 0.125% pancretin and 1 ml of 0.1% collagenase II again, shaken in 37° C. water bath for digestion for 10 min, the supernatant was sucked and transferred to a centrifuge tube, and the supernatant was added with DMEM containing 10% FBS to terminate digestion; the step of shaking and digestion in water bath was repeated for 3-4 times, until the tissue pieces were completely digested; the collected cell suspension was centrifuged under 1000 rpm for 10 min, the supernatant was removed, then a culture medium was added for resuspension; the resuspended cells were inoculated in a cell culture flask, placed in CO2 incubator at 37° C. for incubation for 1.5 h, then the culture medium was sucked out, countered under microscope, then DMEM culture medium containing 10% FBS was used to adjust cell density, inoculated in an amount of $1\times10^4$ to a 96-well plate, placed in 5% CO2 incubator at 37° C. for 24 h, then half medium was replaced, a culture medium containing 0.1% Brdu was supplementally added; then the medium was replaced once per 48 h, and primary cardiomyocytes were obtained after 4 days of cultivation.

Measurement of Cell Inhibition Rate (MTT)

The isolated primary culture of cardiomyocytes was inoculated in an amount of $10^4$ cells per well to a 96-well plate, and the volume of each well was 100 ul (marginal wells were filled with sterile PBS). After being cultivated in 5% $CO_2$ and 37° C. incubator for 4d, they were added with the compound of Formula I of Example 1 in different concentrations (0.3 μM, 1 μM, 3 μM, 10 μM, 30 μM, 100 μM), 3 double-wells were set for each concentration, at the same time, zero setting wells (culture medium, MTT, DMSO), and control wells (culture medium, DMSO) were also set. After continuous inoculation for 48 h, each well was added with 20 ul of MTT solution (5 mg/ml, formulated with PBS (pH=7.4), i.e., 0.5% MTT), and the cultivation was continued for 4 h. After the end of cultivation, culture medium in wells was carefully sucked out. Each well was added with 150 ul of DMSO, shaken at a low speed in a shaking table for 10 min, so that the crystal was sufficiently dissolved. The optical density (OD) value of each well was measured at wavelength of 550 nm by enzyme-linked immunoassay instrument, and each well was repeatedly measured for 5 times and the results were recorded. The results are shown in Table 1.

TABLE 1

Effects of the compound at different concentrations on survival rate of the cardiomyocytes as assayed by the MTT method

| Group | | Inhibitive rate of cardiomyocytes (%) |
|---|---|---|
| Control group | | 100 |
| Compound of Example 1 | 100 μM group | 2.91 ± 1.88 |
| | 300 μM group | 0.76 ± 0.42 |

The results show that the compound of Example 1 at a concentration within 300 μM has no effect on survival rate of normal cardiomyocyte.

Assay of the Activity for Protection of Cardiomyocytes: Activity for Protecting Cardiomyocytes Apoptosis Induced by TG Cardiomyocytes were subjected to the primary culture for 4 days according to the above method, and then added with thapsigargin (TG) to induce apoptosis. The compound of the present invention was added for pretreatment 30 min before inducing apoptosis. The cells were randomly divided into 5 groups: (1) solvent control group (DMSO); (2) TG intervening group (0.4 uM); (3) TG (0.4 uM)+compound intervening group (0.3 uM); (4) TG (0.4 uM)+compound intervening group (1 uM); (5) TG (0.4 uM)+compound intervening group (3 uM). TG was formulated with DMSO, the mother liquid was of 4 mM; and the compound of the present invention was formulated with DMSO, and the mother liquid was of 150 mM. The cell survival rate was measured according to the above MTT method, so as to test the protection effects of the compound of the present invention on the TG-induced cardiomyocytes apoptosis, and the results are shown in Table 2.

TABLE 2

Effects of the compound at different concentrations on TG-induced cardiomyocytes apoptosis as assayed by the MTT method

| Group | | Survival rate of cardiomyocytes (%) |
|---|---|---|
| Control group | | 100 |
| TG intervening group | | 59 ± 1.1 |
| Compound of Example 1 | 0.3 μM group | 76.3 ± 7.6 |
| | 1 μM group | 83.3 ± 7.1 |
| | 10 μM group | 92.2 ± 5.6 |

Note:
the survival rate of the cells = 1 − the inhibition rate of the cells

The experimental results: in comparison with the group added with TG alone, the survival rate of the cardiomyocytes was significantly increased when TG and the compound of Example were added together, indicating that the compound of Example as indicated in table 2 can significantly improve TG-induced apoptosis and has a protection effect on the cardiomyocytes.

Although the specific modes for carrying out the invention have been described in details, those skilled in the art would understand that according to the disclosed teachings, these details could be subjected to various modifications and replacements, and all of these alternations are covered by the protection scope of the present invention. The protection scope of the present invention is determined by the attached claims and any equivalents thereof.

What is claimed is:

1. A compound of Formula I,

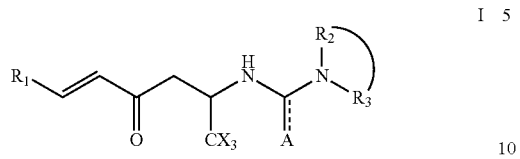

or pharmaceutically acceptable salt or solvate thereof, wherein:

A represents =S, —SR$_4$ or =O;
X represents F, Cl, Br or I;
R$_1$ represents phenyl;
R$_2$, and R$_3$ are attached together to form morpholine; and
R$_4$ represents C$_1$-C$_6$ alkyl.

2. The compound according to claim 1, wherein
R$_4$ represents methyl, ethyl, propyl, isopropyl, butyl or pentyl.

3. The according to claim 1, wherein
X represents Cl; and
R$_4$ represents methyl or ethyl.

4. The compound according to claim 1 which is
(1) (1E)-1-phenyl-5-(1-morpholinylthiocarboxamido)-6,6,6-trichloro-1-ene-3-hexanone, or a pharmaceutically acceptable salt or solvate thereof.

5. A pharmaceutical composition comprising a compound according to claim 1, and a pharmaceutically acceptable carrier, excipient or diluent.

* * * * *